(12) United States Patent
Davis

(10) Patent No.: US 10,765,104 B2
(45) Date of Patent: *Sep. 8, 2020

(54) DISPENSER

(71) Applicant: S. C. Johnson & Son, Inc., Racine, WI (US)

(72) Inventor: Brian T. Davis, Burlington, WI (US)

(73) Assignee: S. C. Johnson & Son, Inc., Racine, WI (US)

( * ) Notice: Subject to any disclaimer, the term of this patent is extended or adjusted under 35 U.S.C. 154(b) by 534 days.

This patent is subject to a terminal disclaimer.

(21) Appl. No.: 15/471,582

(22) Filed: Mar. 28, 2017

(65) Prior Publication Data

US 2017/0196215 A1   Jul. 13, 2017

Related U.S. Application Data

(63) Continuation of application No. 14/230,992, filed on Mar. 31, 2014, now Pat. No. 9,603,352.

(51) Int. Cl.
*A01M 1/20* (2006.01)
*A01M 29/12* (2011.01)
(Continued)

(52) U.S. Cl.
CPC .............. *A01M 29/12* (2013.01); *A01M 1/20* (2013.01); *A01M 1/2022* (2013.01);
(Continued)

(58) Field of Classification Search
CPC .... A01M 1/20; A01M 1/2005; A01M 1/2016; A01M 1/2022; A01M 1/2027;
(Continued)

(56) References Cited

U.S. PATENT DOCUMENTS

| 862,467 | A | * | 8/1907 | Gardner | .................. | A01M 1/14 43/114 |
| 935,428 | A | * | 9/1909 | Stranzenbach | ......... | A01M 1/14 43/114 |

(Continued)

FOREIGN PATENT DOCUMENTS

| AU | 720683 B2 | 6/2000 |
| EP | 1526770 B1 | 9/2006 |

(Continued)

OTHER PUBLICATIONS

International Search Report and Written Opinion, International Application No. PCT/US2015/023485, dated Aug. 31, 2015, 16 pages.

(Continued)

*Primary Examiner* — Darren W Ark
(74) *Attorney, Agent, or Firm* — Quarles & Brady LLP

(57) ABSTRACT

An emanating device includes a substrate with a body having a first portion and a second portion, a foldable member, and first and second hinges along a longitudinal axis of the body and connected to the foldable member. The foldable member is movable between a first state, such that the member is co-planar with the first portion and second portion, and a second state, such that the foldable member is not co-planar with the first portion and the second portion.

20 Claims, 10 Drawing Sheets

(51) Int. Cl.
*A01M 29/00* (2011.01)
*A61L 9/12* (2006.01)

(52) U.S. Cl.
CPC ........ *A01M 1/2027* (2013.01); *A01M 1/2055* (2013.01); *A01M 29/00* (2013.01); *A61L 9/12* (2013.01); *Y10T 428/16* (2015.01)

(58) Field of Classification Search
CPC .. A01M 1/2044; A01M 1/2055; A01M 29/12; A01M 29/00; A01M 1/00; A01M 1/02; A01M 1/10; A01M 1/103
USPC ......... 43/132.1, 124, 131, 107, 122; 239/34, 239/53, 54, 57; 428/542.2, 542.6; 40/124.08, 427, 439, 440
See application file for complete search history.

(56) References Cited

U.S. PATENT DOCUMENTS

| | | | | |
|---|---|---|---|---|
| 1,071,578 A * | 8/1913 | Rese | .......... | A01M 1/14 43/114 |
| 1,112,064 A * | 9/1914 | Gordon | .......... | A01M 1/02 43/114 |
| 1,118,845 A * | 11/1914 | Day | .......... | A01M 1/14 43/114 |
| 1,521,261 A * | 12/1924 | Tschernitschek | ....... | A01M 1/14 43/136 |
| 1,645,715 A * | 10/1927 | Northrup | .......... | A01M 1/14 43/115 |
| 2,073,791 A * | 3/1937 | Graef | .......... | A01M 1/165 43/116 |
| 2,120,204 A * | 6/1938 | Langhorst | .......... | A61L 9/03 239/54 |
| 2,258,683 A * | 10/1941 | Ketterer | .......... | A01M 1/02 43/114 |
| 2,765,579 A * | 10/1956 | Gordon | .......... | A01M 1/2088 43/127 |
| 3,116,077 A * | 12/1963 | Bird | .......... | B42D 1/007 281/15.1 |
| 3,185,394 A * | 5/1965 | Farrell | .......... | A45D 34/00 239/36 |
| 3,432,953 A * | 3/1969 | Pinzke | .......... | G09F 5/00 40/124.06 |
| 3,516,186 A * | 6/1970 | Arlet | .......... | G09F 5/00 40/427 |
| 3,655,129 A | 4/1972 | Seiner | | |
| 3,685,199 A * | 8/1972 | Bradshaw | .......... | A01M 1/14 43/114 |
| 3,729,858 A * | 5/1973 | Bradshaw | .......... | A01M 1/14 43/114 |
| 3,755,958 A * | 9/1973 | Bradshaw | .......... | A01M 1/02 43/114 |
| 3,863,384 A * | 2/1975 | Weatherston | .......... | A01M 1/14 43/114 |
| 4,133,137 A * | 1/1979 | van Adelsberg | ........ | A01M 1/02 229/116 |
| 4,156,321 A * | 5/1979 | Capizzi | .......... | A01M 1/14 43/114 |
| 4,220,281 A * | 9/1980 | Martens, III | ........ | A61B 5/0816 239/57 |
| 4,442,624 A * | 4/1984 | Browne | .......... | A01M 1/02 43/107 |
| 4,484,768 A * | 11/1984 | Norfleet | .......... | B42D 15/02 229/92.8 |
| 4,592,163 A * | 6/1986 | Wilson | .......... | A01M 1/02 206/806 |
| 4,747,539 A * | 5/1988 | Spector | .......... | A61L 9/12 239/45 |
| 4,789,572 A * | 12/1988 | Weaver | .......... | A41G 1/00 156/61 |
| 4,839,144 A * | 6/1989 | Martin | .......... | A01M 1/2066 206/524.3 |
| 4,961,282 A * | 10/1990 | Hoppe | .......... | A01M 1/14 43/114 |
| 4,961,930 A | 10/1990 | Perdelwitz | | |
| 5,003,635 A | 4/1991 | Peterson | | |
| 5,033,674 A * | 7/1991 | Smith | .......... | A61L 9/12 239/34 |
| 5,062,551 A | 11/1991 | Goldstein et al. | | |
| 5,248,537 A | 9/1993 | Giannavola | | |
| 5,384,981 A * | 1/1995 | Cohen | .......... | A01M 1/14 43/114 |
| D359,348 S * | 6/1995 | El-Assir | .......... | D23/366 |
| 5,788,061 A * | 8/1998 | Hammond | .......... | A61L 9/12 206/0.5 |
| 5,788,155 A * | 8/1998 | Martin | .......... | A61L 9/12 239/34 |
| 5,915,948 A * | 6/1999 | Kunze | .......... | A01M 1/145 43/113 |
| 5,961,043 A * | 10/1999 | Samuelson | ........ | A01M 1/2044 239/54 |
| 5,993,843 A * | 11/1999 | Sakurada | .......... | A01M 1/02 424/403 |
| 6,155,002 A * | 12/2000 | Holder | .......... | A01M 1/14 43/114 |
| 6,159,489 A * | 12/2000 | Sakurada | .......... | A01M 1/02 424/403 |
| 6,216,960 B1 * | 4/2001 | Aiba | .......... | A01M 1/2044 239/34 |
| 6,327,813 B1 * | 12/2001 | Ishiwatari | ......... | A01M 1/2055 43/125 |
| 6,360,477 B1 * | 3/2002 | Flashinski | .......... | A01M 1/2044 223/86 |
| 6,419,943 B1 * | 7/2002 | Sakurada | .......... | A01M 1/02 424/409 |
| 6,516,558 B1 * | 2/2003 | Lingren | .......... | A01M 1/02 43/107 |
| 6,534,079 B1 | 3/2003 | Munagavalsa | | |
| 6,557,778 B1 * | 5/2003 | Shiffler | .......... | A01M 1/2055 239/53 |
| 6,575,383 B2 | 6/2003 | Dobler et al. | | |
| 6,582,714 B1 | 6/2003 | Emmrich et al. | | |
| 6,599,525 B2 | 7/2003 | Scamilla Aledo et al. | | |
| 6,783,815 B2 * | 8/2004 | Flohe | .......... | A47G 33/08 428/11 |
| 6,857,579 B2 * | 2/2005 | Harris | .......... | A01M 1/2044 239/211 |
| 6,959,510 B1 * | 11/2005 | Nelson | .......... | A01M 1/04 43/113 |
| 7,007,354 B2 * | 3/2006 | Flohe | .......... | A47G 33/08 29/6.1 |
| 7,051,949 B2 * | 5/2006 | Aiyama | .......... | A01M 1/2055 239/34 |
| 7,055,295 B1 * | 6/2006 | Aiba | .......... | A01M 1/2044 53/451 |
| 7,127,842 B2 * | 10/2006 | Murthy | .......... | G09F 19/02 40/124.08 |
| 7,261,948 B2 * | 8/2007 | Edkins | .......... | A47G 33/08 428/542.6 |
| 7,419,102 B2 | 9/2008 | Harris | | |
| 7,523,577 B2 * | 4/2009 | Majerowski | ........ | A01M 1/2055 239/34 |
| 7,530,503 B2 * | 5/2009 | Caserta | .......... | A01M 1/2044 239/34 |
| 7,676,985 B1 * | 3/2010 | Perkins | .......... | A01M 1/026 43/114 |
| 7,926,734 B2 * | 4/2011 | Dobler | .......... | A61L 9/12 239/52 |
| 7,935,407 B2 * | 5/2011 | Chen | .......... | A47G 33/08 428/12 |
| 7,980,507 B2 | 7/2011 | Patrick | | |
| 8,062,598 B2 * | 11/2011 | Bertassi | .......... | A01M 1/2044 239/58 |
| 8,178,114 B2 | 5/2012 | Klausen et al. | | |
| 8,240,081 B2 * | 8/2012 | Cuellar Bernal | ..... | A01M 1/145 43/107 |
| 8,480,960 B2 | 7/2013 | Wheatley et al. | | |

(56) References Cited

U.S. PATENT DOCUMENTS

| | | | | |
|---|---|---|---|---|
| 8,622,206 B2* | 1/2014 | Miller | .................... | B65D 75/20 206/63.5 |
| 8,793,927 B2* | 8/2014 | Winkler | .................. | A01M 1/14 43/107 |
| D722,376 S * | 2/2015 | Davis | .......................... | D23/366 |
| 9,248,210 B2* | 2/2016 | Kunesh | .................... | A61L 9/12 |
| 9,327,043 B2* | 5/2016 | Olchovy | ................... | A61L 9/12 |
| 9,603,352 B2* | 3/2017 | Davis | .......................... | A01M 29/12 |
| 9,936,683 B2* | 4/2018 | Saguchi | .................. | A01M 1/02 |
| 2003/0001023 A1* | 1/2003 | Simms | ................. | A01M 1/2055 239/34 |
| 2003/0034403 A1* | 2/2003 | Baxter | ................ | A01M 31/008 239/36 |
| 2003/0094504 A1* | 5/2003 | Rymer | ................. | A01M 1/2044 239/34 |
| 2005/0144831 A1* | 7/2005 | Knauf | .................... | A01M 1/02 43/107 |
| 2005/0199740 A1* | 9/2005 | Harris, Jr. | ........... | A01M 1/2044 239/34 |
| 2005/0246943 A1* | 11/2005 | Neumann | ........... | A01M 1/2055 43/132.1 |
| 2006/0102737 A1* | 5/2006 | Harmon | .............. | A01M 1/2055 239/6 |
| 2006/0269769 A1* | 11/2006 | Sater | ........................ | A63H 1/00 428/542.2 |
| 2008/0011871 A1* | 1/2008 | Sexton | ................ | A01M 1/2044 239/55 |
| 2008/0086932 A1* | 4/2008 | Cook | ...................... | A01M 1/02 43/114 |
| 2008/0105760 A1 | 5/2008 | Sheffield et al. | | |
| 2009/0183419 A1* | 7/2009 | Harris | .................... | A01M 1/14 43/114 |
| 2011/0278370 A1 | 11/2011 | Glydon | | |
| 2012/0055075 A1* | 3/2012 | Winkler | .................. | A01M 1/02 43/114 |
| 2013/0111802 A1* | 5/2013 | Oehlschlager | .......... | A01M 1/14 43/114 |
| 2013/0168463 A1 | 7/2013 | Dobler et al. | | |
| 2014/0027530 A1* | 1/2014 | Cao | ......................... | A61L 9/042 239/6 |
| 2014/0083001 A1* | 3/2014 | Alcov | ................... | A01M 29/24 47/20.1 |
| 2014/0123539 A1 | 5/2014 | Saguchi et al. | | |
| 2014/0141051 A1* | 5/2014 | Swanson | ................ | A01N 65/00 424/409 |
| 2015/0001308 A1* | 1/2015 | Meier | .................... | A01N 25/18 239/6 |
| 2015/0021408 A1* | 1/2015 | Matthews | ............... | A61L 9/127 239/34 |
| 2015/0237842 A1* | 8/2015 | Thuis | .................... | A01M 1/103 43/114 |
| 2018/0117206 A1* | 5/2018 | Vega | ................... | A01M 1/2055 |

FOREIGN PATENT DOCUMENTS

| | | | | |
|---|---|---|---|---|
| EP | 2361202 A1 | | 8/2011 | |
| EP | 2361202 B1 | * | 8/2015 | |
| GB | 2039740 A | * | 8/1980 | .......... A01M 1/2055 |
| GB | 2039740 A | | 8/1980 | |
| JP | 11164766 A | * | 6/1999 | |
| JP | 11164766 A | | 6/1999 | |
| JP | 2004-283108 A | | 10/2004 | |
| JP | 2005-298362 A | | 10/2005 | |
| KR | 20040058008 A | * | 7/2004 | .......... A01M 1/2055 |
| KR | 20110053412 A | * | 5/2011 | .......... A01M 1/2055 |
| WO | 0207512 A1 | | 1/2002 | |
| WO | WO-0207512 A1 | * | 1/2002 | .......... A01M 1/2044 |
| WO | 2005046332 A1 | | 5/2005 | |
| WO | 2005053390 A1 | | 6/2005 | |
| WO | 2006088139 A1 | | 8/2006 | |
| WO | 2006134353 A1 | | 12/2006 | |
| WO | 2008012507 A1 | | 1/2008 | |
| WO | WO-2008012507 A1 | * | 1/2008 | .......... A01M 1/2055 |
| WO | WO-2009002435 A2 | * | 12/2008 | .......... A01M 1/2055 |
| WO | 2014018594 A1 | | 1/2014 | |
| WO | WO-2014018594 A1 | * | 1/2014 | |

OTHER PUBLICATIONS

First Office Action issued in corresponding Chinese Application No. 201580022315.9, dated Sep. 11, 2018, 14 pages.

* cited by examiner

DISPENSER

CROSS REFERENCE TO RELATED APPLICATIONS

This application claims priority to U.S. patent application Ser. No. 14/230,992 filed on Mar. 31, 2014.

REFERENCE REGARDING FEDERALLY SPONSORED RESEARCH OR DEVELOPMENT

Not applicable

SEQUENCE LISTING

Not applicable

BACKGROUND OF THE INVENTION

1. Field of the Background

The present invention relates generally to a passive volatile material dispenser.

2. Description of the Background

Various volatile material dispensing devices are known that generally include a reservoir that holds a volatile material and may include a housing or support structure to retain the reservoir. These devices typically either allow passive diffusion of the volatile material to occur without the aid of a dispensing mechanism or enhance and/or facilitate the release of the volatile material using a dispensing mechanism. Often prior passive dispensers incorporate volatile materials into waxes and gel systems that dissipate during use. However, such media tend to be fragile and are susceptible to impact, extreme temperatures, and changes in humidity.

One answer to the fragility of such dispensers is to use a more robust medium, such as cellulose charged with one or more volatile actives. For example, one type includes a pre-scented or custom card insert made of paper (e.g., blotting paper), a non-woven porous material, or a synthetic carrier material such as extruded polyethylene or molded polystyrene that holds a volatile active. The card may be square or rectangular with parallel perforation lines extending between opposite sides of the card to allow the card to be easily rolled or formed to a size to be inserted into a roll of paper towels or toilet paper.

Another example includes an insect control article that has a substrate impregnated with a passively emanated active insect control ingredient selected from transfluthrin or other pyrethroids. The substrate may be paperboard, an open pore cellulosic material, coiled corrugated paper, and the like. The article may include hanger means and is preferably positioned within a room or similar space with air movement.

However, such prior art designs are poorly designed for maximizing emissions. For example, monolithic or minimally porous designs inhibit air flow through the dispenser. Similarly, such designs may only dispense volatile materials in a unidirectional fashion. Still further, such designs typically have static emission rates.

Attempts to improve upon these prior designs, for example, by increasing surface area to improve emission rates, have typically led to more complex dispensers. For example, certain dispenser devices are designed such that they can be folded and unfolded into three dimensional structures with one or more elements to repel flying insects, like mosquitoes. The devices are provided with a plurality of body sheets attached to each other at a plurality of locations. When fully open, the device presents a plurality of chambers with functional surfaces that may be treated with substances that attract, repel, or capture flying insects.

However, such complex dispensers require more materials and increased manufacturing steps for construction. It follows that complex dispensers are more expensive due to greater material costs due to multiple piece construction and greater labor costs due to their multiple step manufacture. Moreover, these complex dispensers create significant amounts of scrap material due to the multiple component pieces that have different shapes and sizes. There is a need, therefore, for passive dispensers that maximize the dispenser surface area exposed to air flow during use, without requiring unnecessary waste of materials and excessive manufacturing steps.

SUMMARY OF THE INVENTION

According to one aspect, an emanating device includes a substrate comprising a body having a first portion and a second portion, a foldable member, and first and second hinges along a longitudinal axis of the body and connected to the foldable member. The foldable member is movable between a first state, such that the foldable member is co-planar with the first portion and second portion, and a second state, such that the foldable member is not co-planar with the first portion and the second portion.

According to another aspect, an emanating device includes a substrate comprising a first portion, a second portion, and a foldable member having a first arm and a second arm. The first portion and the second portion include first and second hinges, respectively, co-axial with a longitudinal axis. In a first state the first arm is co-planar with the first portion and the second arm is co-planar with the second portion. In a second state, the first arm is not co-planar with the first portion and the second arm is not co-planar with the second portion.

According to a further aspect, an emanating device includes an absorbent substrate comprising a body having a porous cellulosic material for the absorption of a volatile active, and further including a first portion and a second portion. The substrate also includes first and second hinges provided on a longitudinal axis of the body and connected to a foldable member along a fold line thereof. The foldable member is movable between a first state, such that the foldable member is co-planar with the first portion and the second portion, and a second state, such that the foldable member is not co-planar with the first portion and the second portion.

BRIEF DESCRIPTION OF THE DRAWINGS

Other aspects and advantages of the present invention will become apparent upon reading the following detailed description and upon reference to the drawings in which.

DETAILED DESCRIPTION OF THE INVENTION

Figure 1:
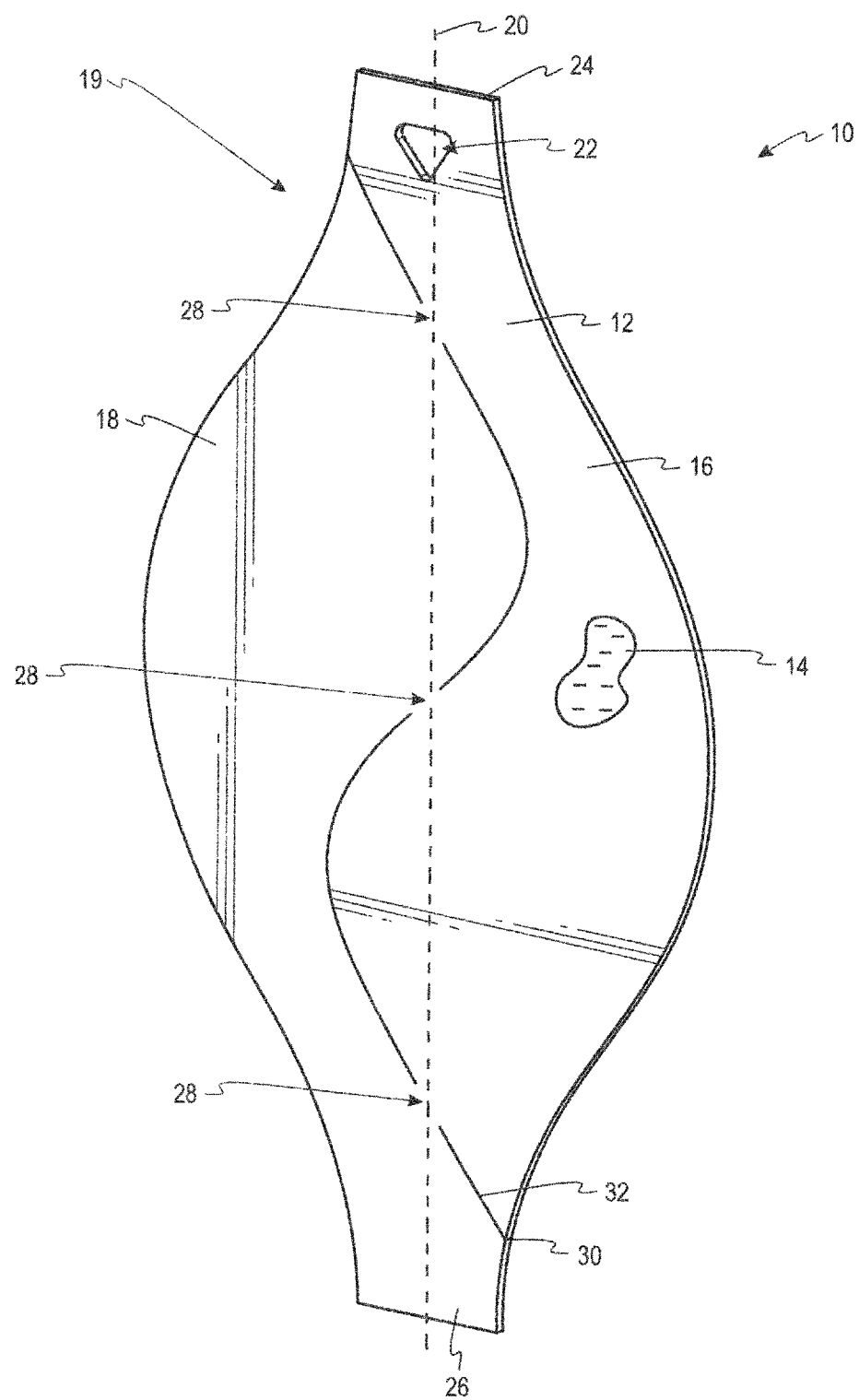
FIG. 1 is an isometric view of a front, top, and left side of a dispenser in a first state.

As depicted in FIGS. 1 to 13A, a dispensing device 10 (e.g., a volatile material dispenser) generally includes a substrate 12 and a volatile material 14 disposed on and/or in the substrate. The dispensing device 10 is adapted to passively dispense the volatile material 14 when exposed to the air and may have increased rates of emission of the volatile material when air flows through and/or around the substrate 12. The substrate 12 includes a first wall portion 16 and a second wall portion 18 attached to the first wall portion along a central axis 20. The first wall portion 16 and the second wall portion 18 comprise a body 19 of the substrate 12. The substrate 12 may also include one or more apertures 22 of any shape to permit the dispensing device 10 to be hung, for example, from a wall hanger display prior to use or another hanging location when in use to increase air flow around and/or through the dispenser. Additionally, a string or similar device (not shown) may be provided through the aperture 22 to assist in hanging the dispensing device 10. In one embodiment, the aperture 22 is centered along the central axis 20 of the dispensing device 10, though the aperture may be disposed in another location.

The dispensing device 10 further includes a first grasping portion 24 and a second grasping portion 26 located on the first 16 and second 18 wall portions, respectively. The first 24 and second 26 grasping portions are disposed such that they are centered on the central axis 20 of the dispensing device 10. The first wall portion 16 may be attached to the second wall portion 18 by various means, such as one or more hinges 28. While three hinges 28 are shown in the embodiment depicted in FIGS. 1-10, more or fewer hinges are contemplated herein (e.g., see FIGS. 11-12A). In some embodiments, the substrate 12 may include two hinges 28 opposite one another and coincident with a fold line.

The substrate 12 is designed to carry the volatile material 14, whether on a surface thereof and/or absorbed therein, and release it into the ambient environment once exposed thereto. In some embodiments, the substrate 12 comprises paper board. In one embodiment, the substrate 12 includes a volatile active-permeable material or a porous material, such as a cellulose fiber-containing substrate. Cellulose fiber-based substrates may include an amount of cellulose by weight ranging from about 50% to about 99%, or about 75% to about 99%, or about 95% to about 99%, or about 97.5% to about 98.5%, or more or less. Similarly, cellulose fiber-based substrates may include an amount of a secondary material by weight ranging from about 1% to about 50%, about 1% to about 25%, or about 1% to about 5%, or about 1.5% to about 2.5%, or more or less. Secondary materials include, for example, binders, pigments, polymers, resins, dyes, combinations thereof, and other materials known in the art. In one embodiment, a cellulose fiber-based substrate may have about 98.5% cellulose and about 1.5% wet strength polyamide resin.

In one embodiment, cellulosic materials, such as paperboard may be used. Additional substrate materials contemplated include crepe paper, printer paper, A4 paper, and other cellulosic materials. Additional examples of materials contemplated for the substrate 12 include plastics, polymers, fabrics, non-woven substrates, such as a PET non-woven substrate, and/or combinations thereof. Additionally, the substrate 12 may include combinations of manufactured, natural, and recycled or reclaimed materials. It is further contemplated that the substrate 12 may include a laminate composed of two or more layers of materials, wherein the laminate may include only volatile active-permeable materials or combinations of volatile active-permeable and impermeable materials, such as a metal or plastic layer.

In one embodiment, the substrate 12 may have a flat, smooth appearance. In another embodiment, however, the substrate 12 may have various textures and/or surface patterns. For example, the substrate 12 may have a rough surface, a smooth surface, a channeled surface, and combinations thereof that may increase surface area and/or the rate of emanation of the volatile material 14 (or volatile composition, which is used interchangeably with volatile material herein) associated therewith.

Further criteria that may be relevant for choosing a substrate 12 include the thickness or caliper of the substrate. For example, the substrate 12 may have a thickness (±10%) of about 0.15 millimeters (mm), or about 0.3 mm, or about 0.4 mm, or about 0.5 mm, or about 1 mm, or about 2 mm, or about 3 mm, or about 5 mm, or about 10 mm. In addition, the basis weight of cellulosic materials may be of interest when choosing such substrates. For example, a basis weight (±10%) of about 250 grams per square meter (gsm), or about 300 gsm, or about 330 gsm may be desirable. Further, the rapidity of a cellulosic substrate may be considered. For example, a rapidity (±10%) ranging from about 30 to 50 milliliters per minute (ml/minute), or about 40 to 60 ml/minute, or about 50 to 70 ml/minute, or about 70 to 100 ml/minute, or a rapidity of about 50 ml/minute, or about 60 ml/minute, or about 70 ml/minute, or about 100 ml/minute may be desirable. Another factor to be considered for cellulosic substrates includes wet burst strength. For example, a desirable substrate may have a wet burst (±10%) of about 180 centimeters $H_2O$, or about 215 centimeters $H_2O$, or about 250 centimeters $H_2O$, or about 280 centimeters $H_2O$.

Rigidity or stiffness of a substrate may be a further criterion for consideration in choosing a substrate. Appropriate rigidity may aid in the appearance and stability of the substrate by reducing the amount of curl of the substrate when impregnated with a composition and/or when exposed to humid conditions. Similarly, in one embodiment, it is preferable to use a substrate with sufficient rigidity such that the first wall portion 16 and the second wall portion 18 substantially maintain their form or shape when the dispensing device 10 is converted from the first state to the second state.

One measure of stiffness is Taber Stiffness or the bending moment (represented in gram-centimeters (g-cm) or milli-Newton meters (mN*m)). For cellulosic substrates, these measurements may be taken along the machine direction (MD) and cross machine direction (CD) orientations of the cellulosic fibers of the substrate. For example, minimal bending moments for a desirable substrate may have a range (±10%) of about 5 to about 10, or about 10 to about 25, or about 20 to about 100, or about 50 to about 175, or about 100 to about 225, or about 150 to about 275, or about 200 to about 325 g-cm or greater.

By dosing or coating the substrate 12 with an appropriate composition, air encountering the dispensing device 10 will acquire a portion of the volatile material 14 thereon and/or therein and dispense it from the dispensing device. Suitable volatile materials/actives may include, for example, insect repellents or insecticides. Alternatively, any other volatile material known to those skilled in the art may be used.

In one embodiment, the insect control active may include D-teflumethrin, transfluthrin, prallethrin, vaporthrin, metofluthrin, tefluthrin, esbiothrin, other synthetic pyrethroids, and combinations thereof. In another embodiment, the insect control active may include insect repellents, such as, for example, mosquito repellents. The composition may solely include an insect control active, or may further include an oil-based and/or water-based carrier, a hydrocarbon, an alcohol, for example, ethanol, or other solvent or carrier, and combinations thereof. It is contemplated that one or more fragrances may be used as "use up" indicators, such that when a user can no longer perceive the scent of the fragrance (s), the strength of the insect control active is no longer effective for its intended purpose and a new device is required or the device must be "recharged" with another dose of the composition or replaced. In this embodiment, the emanation rate of the fragrance(s) and that of any volatile material are substantially the same. Additional use-up cues may include individual or combinations of appearing and disappearing inks and the like. Any fragrance may be used herein including, for example, a floral scent, a fresh scent, a lavender scent, a eucalyptus scent, a pine scent, a spice scent, and combinations thereof.

In one embodiment, a volatile composition may include a fragrance, a carrier, and volatile active/active ingredient in an amount as depicted in Table No. 1.

TABLE NO. 1

| Composition. | |
|---|---|
| Component | Approximate Wt % (±10%) |
| Fragrance | 75 to 97% |
| Carrier | 0 to 17% |
| Volatile active | 3 to 8% |

In another embodiment, the components of a volatile composition, once combined, may be thoroughly mixed and dosed onto the substrate 12 in any desired amount. For example, the compositions may be dosed in an amount ranging from about 1 to 2 grams, or about 2 to 4 grams, or about 4 to 8 grams, or about 8 to 20 grams, or about 20 to 50 grams, or about 1 gram, or about 2 grams, or about 4 grams, or about 8 grams, or about 10 grams, or in an amount of about 20 grams, or about 50 grams per cellulose substrate measuring about 9 centimeters by about 17.5 centimeters and having a caliper width of about 1 millimeter.

The substrate 12 is preferably capable of holding a dose of the volatile composition containing the volatile material in a relatively even distribution thereon and also capable of allowing evaporation in response to the air flow equally from all exposed surfaces. The substrate 12 may also allow for wicking of the active ingredient following dosing to ensure efficient distribution throughout the substrate 12. Dosing/loading may be accomplished by dropping, spraying, printing, soaking or other conventional delivery of a liquid composition to the substrate 12.

The dispensing device 10 may be employed in a first state, as shown in FIGS. 1-4 where the first wall portion 16 and the second wall portion 18 of the substrate 12 are substantially coplanar. As illustrated in FIG. 2A, the substrate 12 includes the central axis 20 along a major length of the dispensing device 10 and an axis W along a major width of the dispensing device. Further, an axis Z is provided orthogonally to the axes 20 and W. In the first state, a plane A defining a front surface of the first wall portion 16 is parallel to axes 20 and W. Similarly in the first state, a plane B defining a front surface of the second wall portion 18 is parallel to axes 20 and W, and therefore, is coplanar with plane A. When the dispensing device 10 is placed in the second state, one of the first wall portion 16 or the second wall portion 18 may be characterized as still being parallel to the axes 20 and W, whereas the other wall portion would no longer be parallel thereto.

The dispensing device 10 may be maintained in the first state until a user grasps the first grasping portion 24 and the second grasping portion 26 and moves (e.g., twists, pivots, or rotates) the dispensing device causing the first wall portion 16 and the second wall portion 18, and therefore planes A and B, respectively, to move relative to one another about the central axis 20 to create a second state with a configuration where the first wall portion and the second wall portion are substantially not coplanar, as is shown in FIGS. 5-9. FIG. 9, in particular, illustrates how a user may grasp the first grasping portion 24 and second grasping portion 26 and twist the dispensing device 10 to convert it from the first to the second state. Only one of the first wall portion 16 and the second wall portion 18 need be moved to obtain the configuration where the first wall portion and the second wall portion are substantially not coplanar. Alternatively, both the first wall portion 16 and the second wall portion 18 may be moved to create the configuration where the first wall portion 16 and the second wall portion 18 are substantially not coplanar. Either of the first wall portion 16 or the second wall portion 18 may be moved clockwise or counterclockwise about the central axis 20 relative to the unmoving wall portion. Alternatively, both the first wall portion 16 and the second wall portion 18 may be moved in opposite directions (e.g., one moving clockwise and the other moving counterclockwise).

In the second state, the dispensing device 10 has a substantially triangular configuration such as seen in FIGS. 5-9, where the first wall portion 16 and the second wall portion 18 are substantially not coplanar. As shown in FIG. 8, in the second state plane A of the first wall portion 16 may remain parallel with axes 20 and W, whereas plane B of the second wall portion 18 may now be parallel with axes 20 and Z, and orthogonal to plane A. Plane A and plane B need not be perpendicular to one another to be not coplanar, and indeed any degree of variation of either plane A or B with respect to the other is contemplated to constitute a configuration in the second state.

In one embodiment, the dispensing device 10 may include one or more attachment point(s) 30 that join the first wall portion 16 and the second wall portion 18 at a location anywhere along a seam 32 exclusive of the central axis 20. The attachment point 30 helps to maintain the dispensing device 10 in the first state until a user decides to convert the dispensing device into the second state by twisting the dispensing device to break the attachment point. The attachment point 30 may be formed by an adhesive, a continuity of the substrate material, or any other chemical or mechanical based attachment means known to one of skill in the art. Further, the attachment point(s) 30 may additionally, or alternatively, comprise a conventional perforated portion(s) or tear strip as known to one of skill in the art.

In the second state, the first 16 and second 18 wall portions may be separated along the seam 32 to create one or more void spaces 34 therebetween to increase the effective surface area of the dispensing device 10. The void spaces 34 allow for greater air flow through the dispensing device 10 and an increased rate of emanation of the volatile material 14 into the environment.

Figure 2:
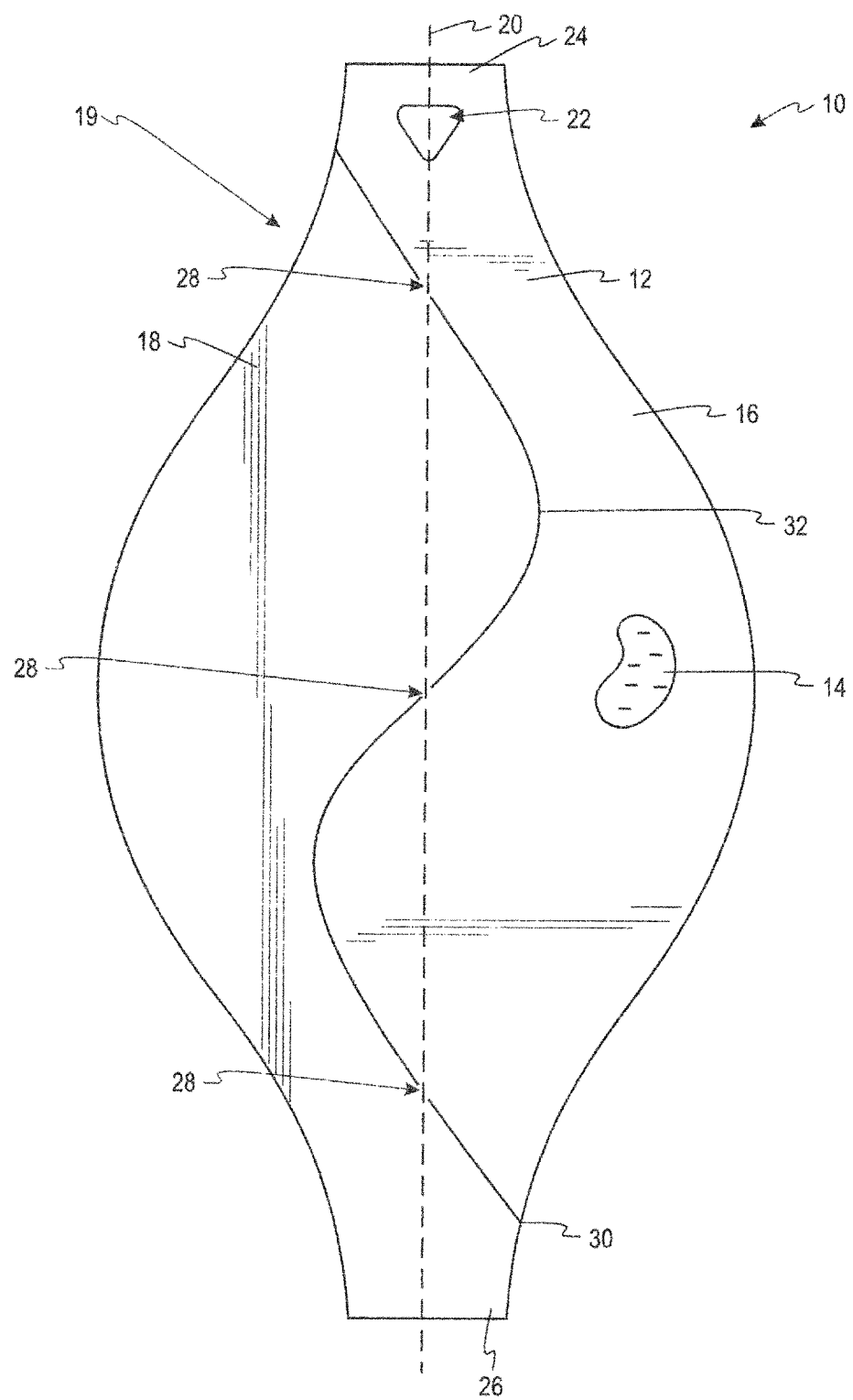
FIG. 2 is a front elevational view of the dispenser of FIG. 1.
Figure 2A:
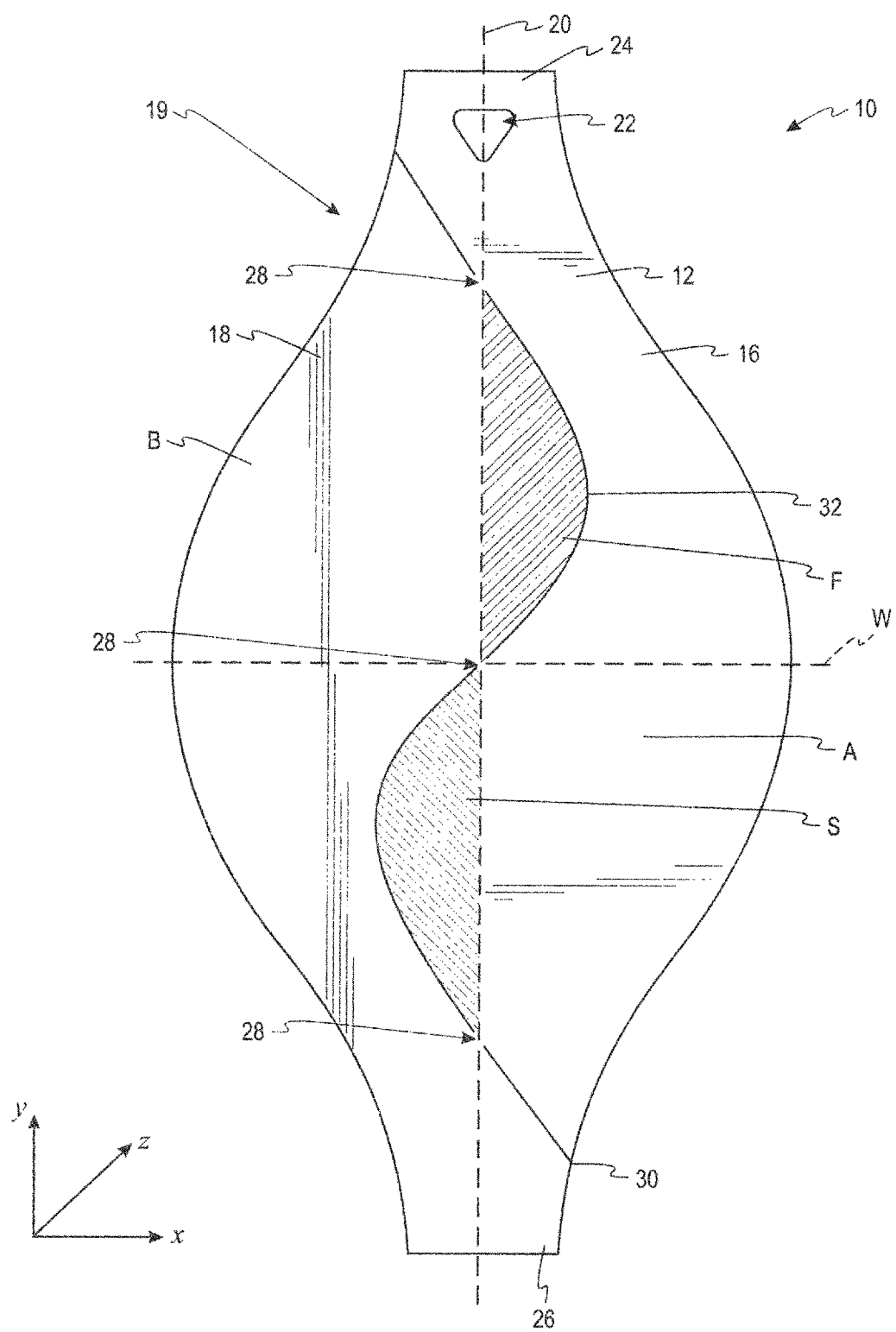
FIG. 2A is a front elevational view of the dispenser of FIG. 1 according to another embodiment.
Figure 4:
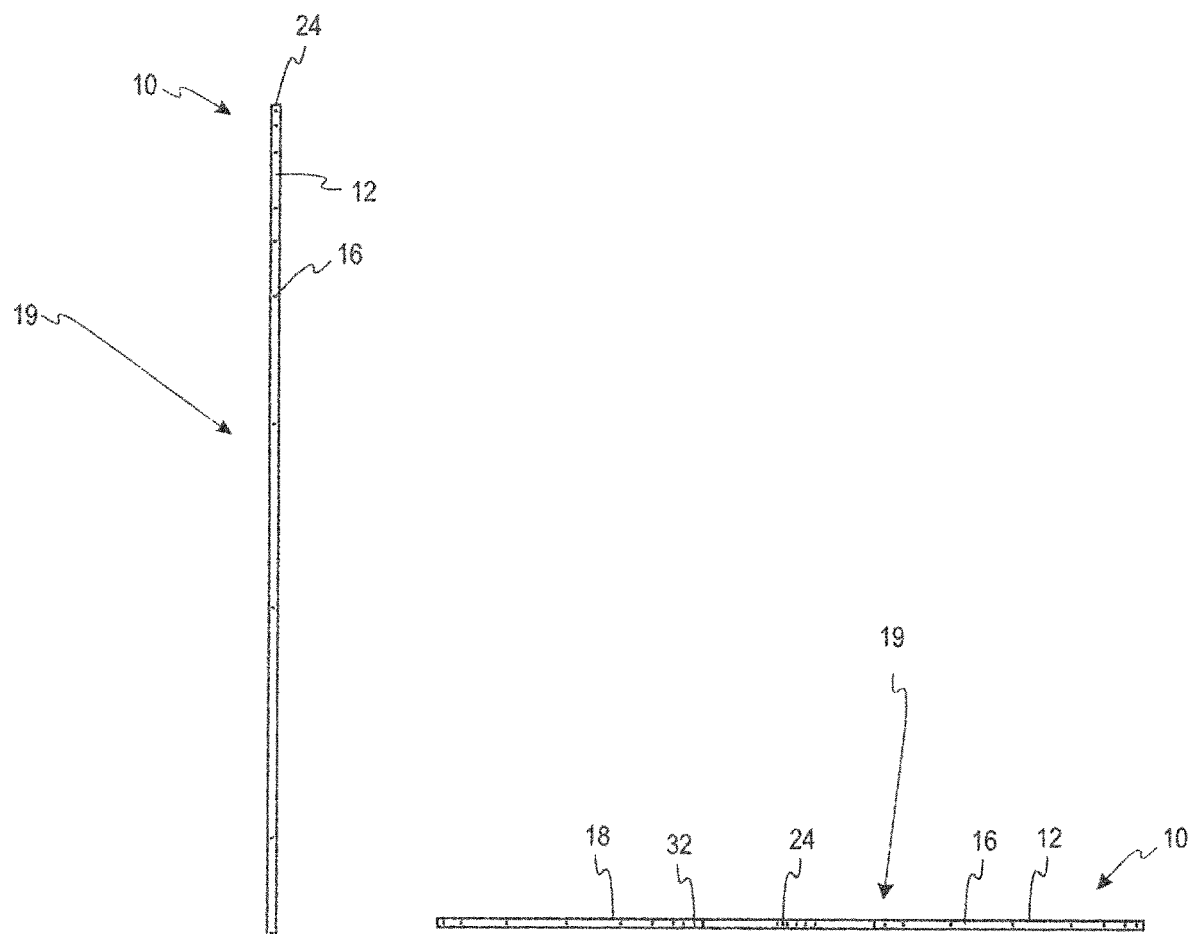
FIG. 4 is a top plan view of the dispenser of FIG. 1.
Figure 3:
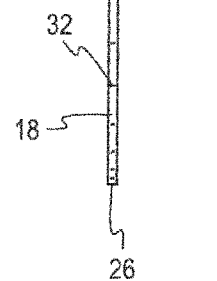
FIG. 3 is a left side elevational view of the dispenser of FIG. 1.
Figure 5:
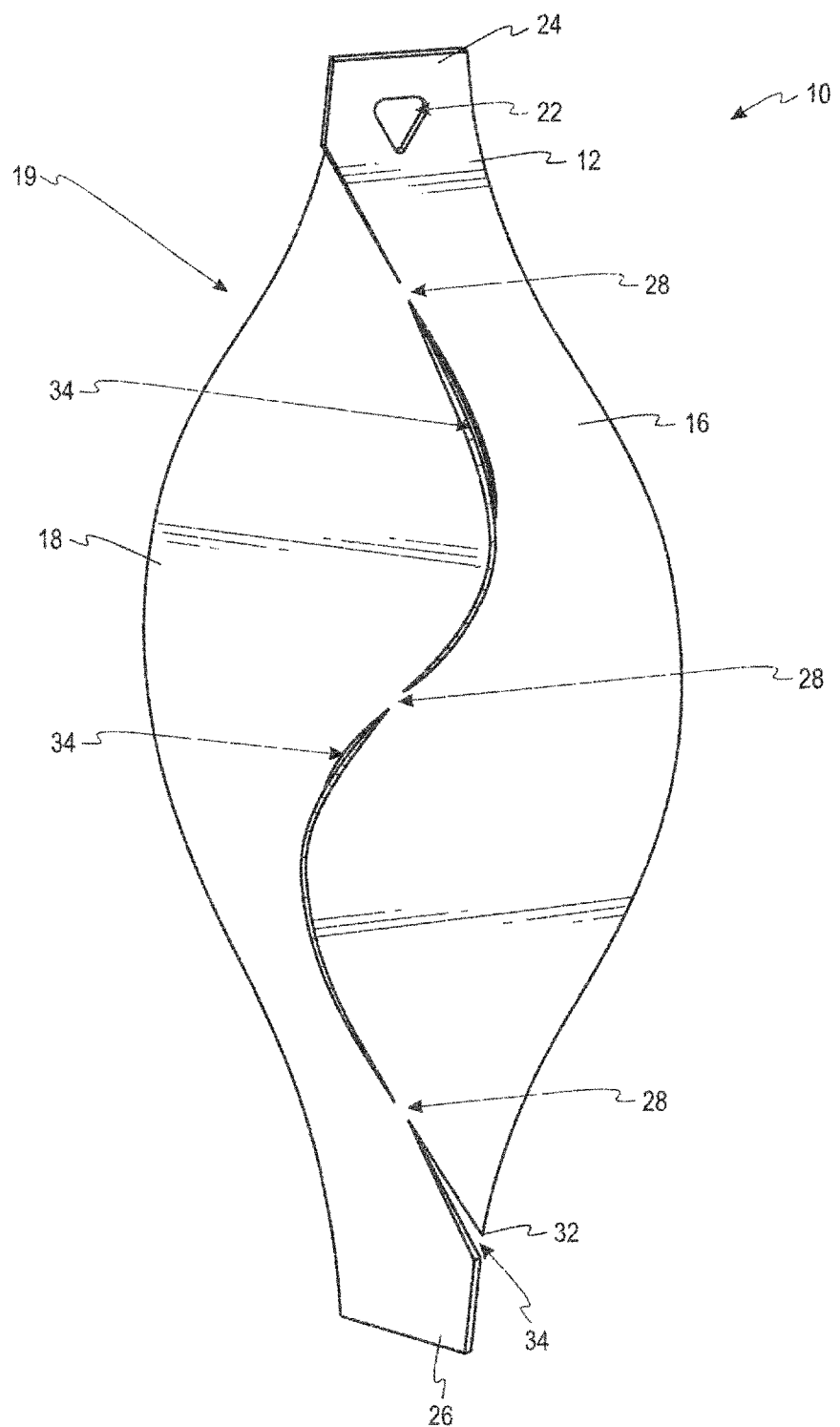
FIG. 5 is an isometric view of a front, top, and left side of the dispenser of FIG. 1 in the second state.
Figure 6:
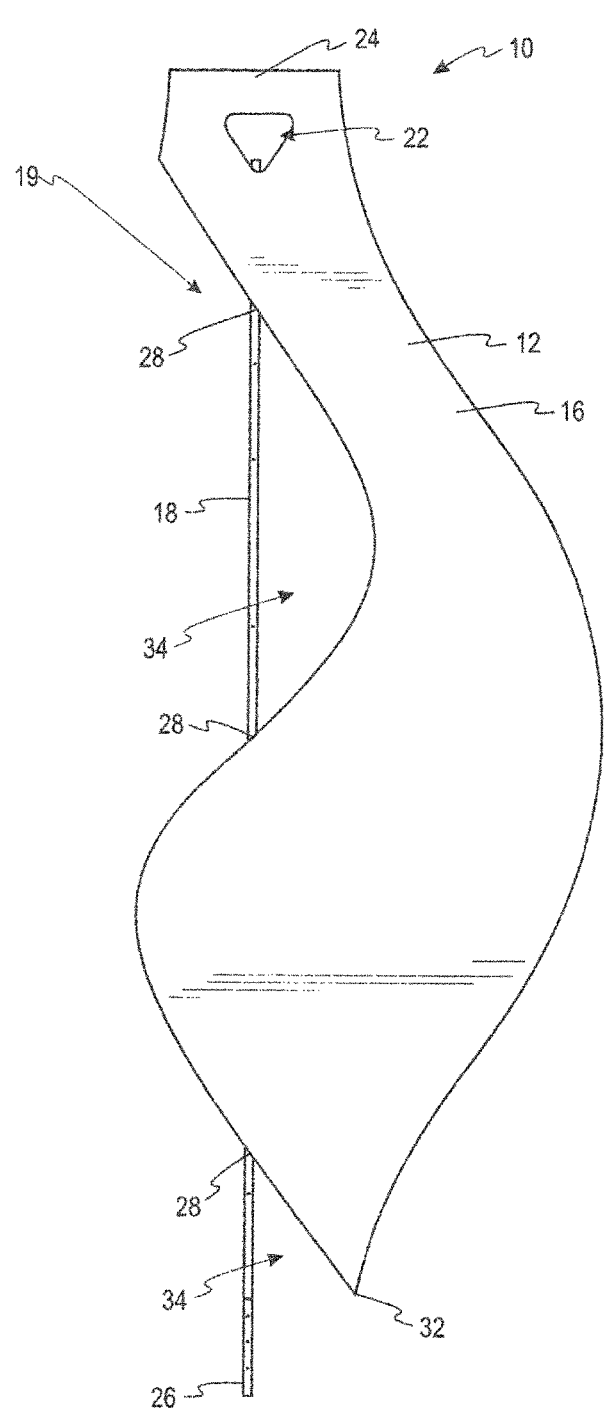
FIG. 6 is a front elevational view of the dispenser of FIG. 5.
Figure 7:
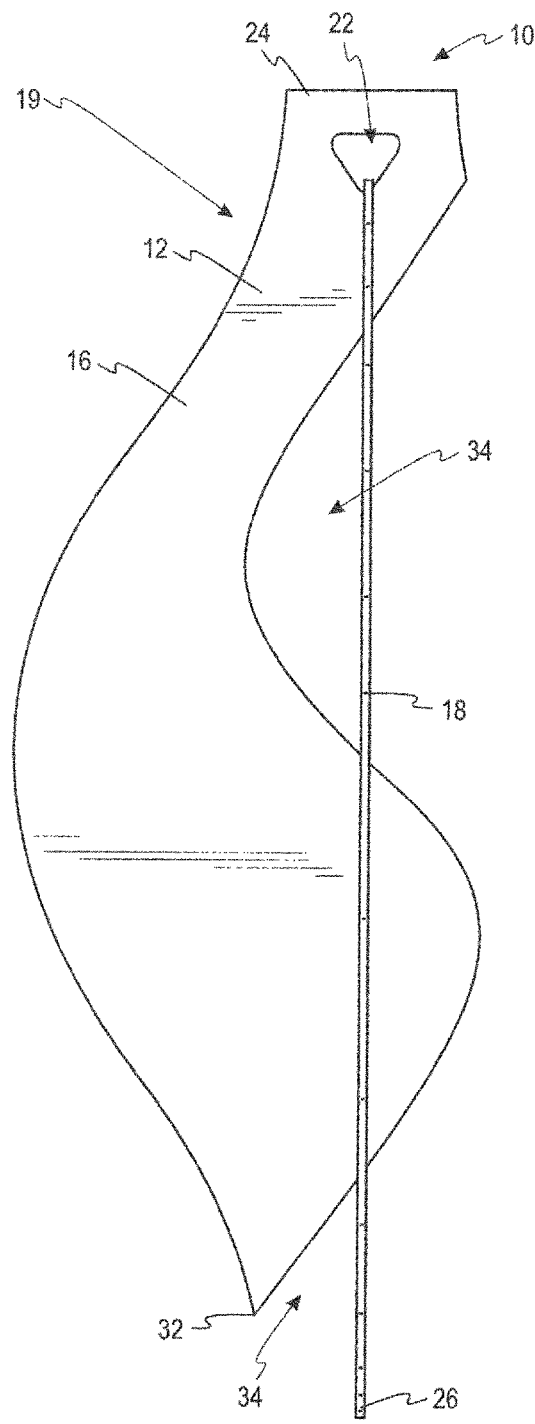
FIG. 7 is a rear elevational view of the dispenser of FIG. 5.
Figure 8:
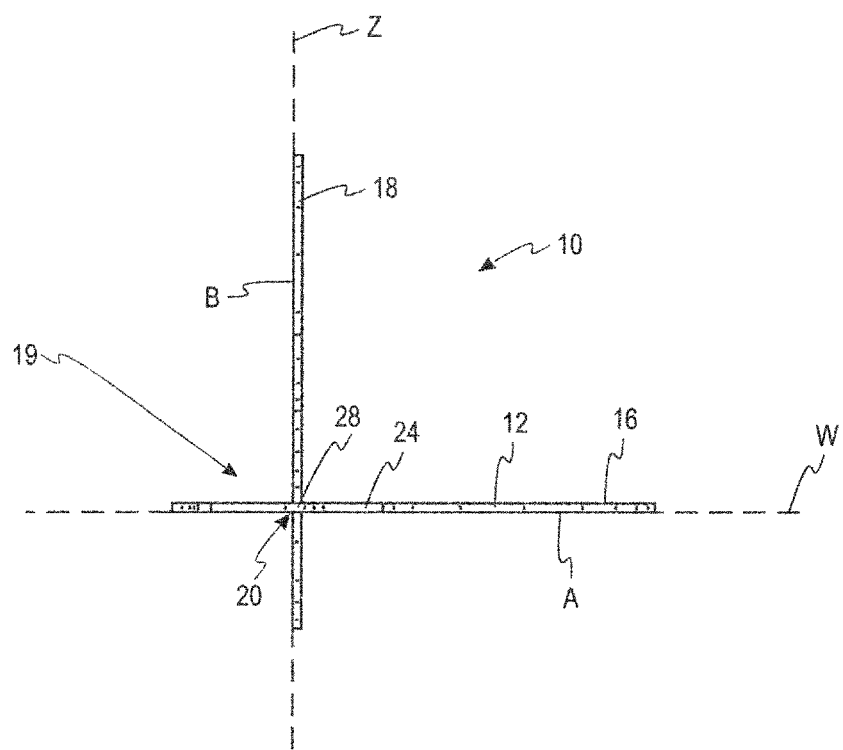
FIG. 8 is a top plan view of the dispenser of FIG. 5.
Figure 9:
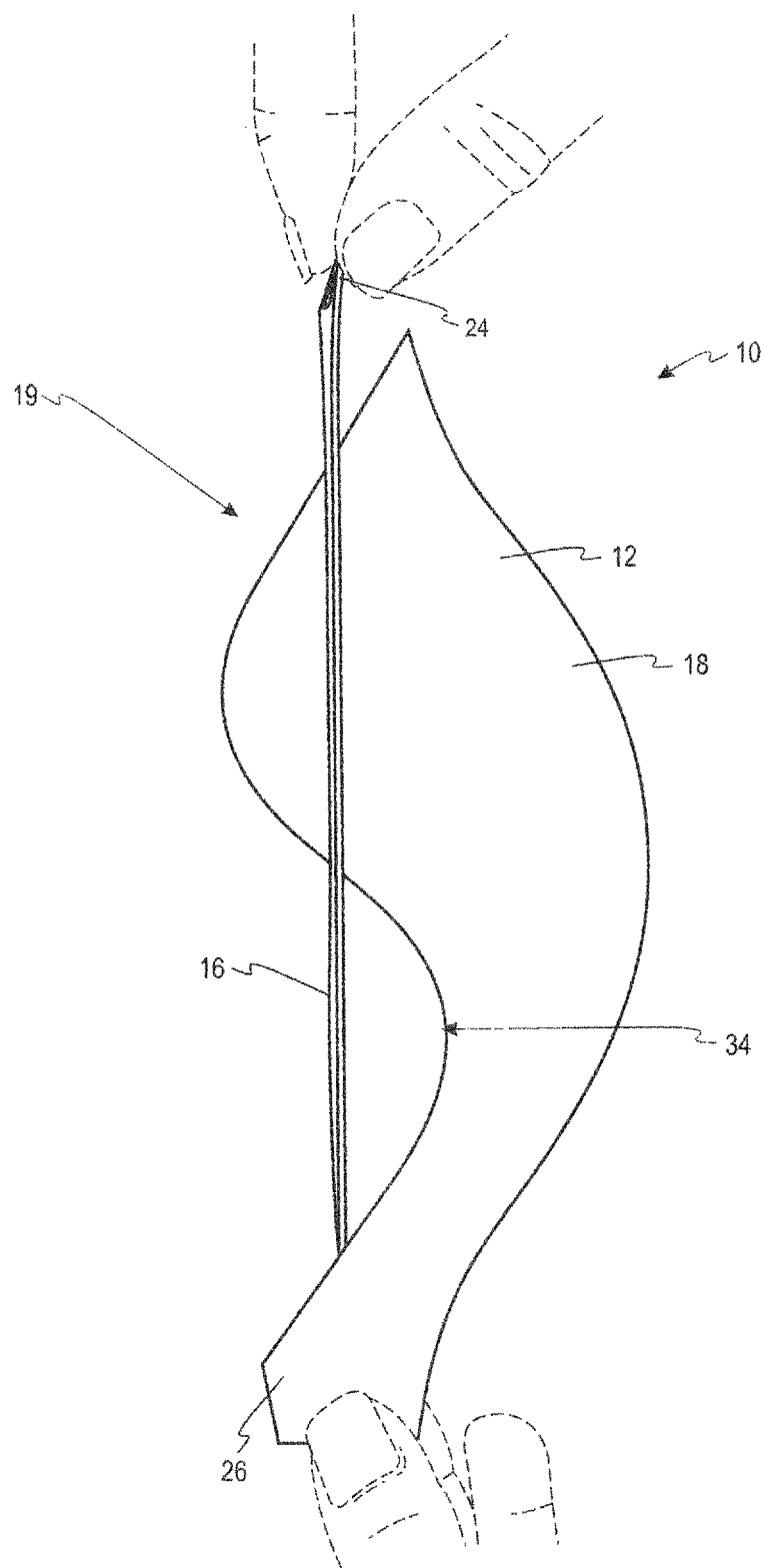
FIG. 9 is a rear elevational view of the dispenser of FIG. 5 converted into a second state by a user grasping first and second grasping portions.

In one embodiment, the substrate 12 may be of any size or shape. In another embodiment, the dispensing device 10 shape conveys an aesthetically pleasing concept of balance. This sense of balance is achieved, in part, by a portion of at least one of the first wall portion and the second wall portion 18 spanning the central axis 20, as seen in FIG. 2A. Here, each of the first 16 and second 18 wall portions has some percentage of its surface area, represented by shaded regions F and S, respectively, on either side of the central axis 20 when viewed in the first state. For example, the regions F and S may separately represent at least about 1%, or about 5%, or about 10%, or about 25%, or about 50%, or more or less, of the surface area of the corresponding wall portion that spans the central axis 20 to convey the concept of balance to a user.

In another embodiment, the dispensing device 10 of the present disclosure may be sold in a package in the first state where the first 16 and second 18 wall portions are substantially planar. Any number of dispensing devices 10 may be included in the packaging, such as one, three, ten, and more or fewer. Further, the packaging may be made of any material that preserves the volatile material 14 within the substrate 12 during shipping and storage (for example, is impervious to the volatile material), such as a cellulosic material, a plastic material, metal material, and combinations thereof. Moreover, the packaging may be of any useful and/or aesthetic shape or configuration known to one skilled in the art, such as a pouch, a bag, a box, a laminated structure, and the like.

In one embodiment, a user may initiate use of a dispensing device 10, for example, a mosquito repellent card, by opening a pouch containing one or more dispensers and removing the dispensing device from the packaging. Thereafter, the dispensing device 10 may be retained in a first state or converted from the first state to a second state to increase volatile material 14 emission. Alternatively, a string or similar item may be inserted through the aperture 22 to hang the dispensing device 10 in a room. In some embodiments, the string or similar item may already be provided in an attached manner to the dispensing device 10 upon removal of the dispensing device from the package. Upon deployment in a room, a dispensing device 10 may require a period of time to reach full strength. For example, it may require about 4, or about 6, or about 8 hours to reach full strength.

Dispensing devices 10 of the present disclosure may be used in an interior space or an exterior space. For example, a dispensing device 10 may be effective against mosquitoes in a room having a size of about 3× about 3 meters, or about 4× about 4 meters, or about 5× about 5 meters, or more or less. Further, dispensing devices 10 of the present disclosure may have an effective duration of continuous use of about 1 day, or about 2 days, or about 4 days, or about 7 days, or about 2 weeks, or about 1 month, or about 2 months, or more or less.

Figure 10:
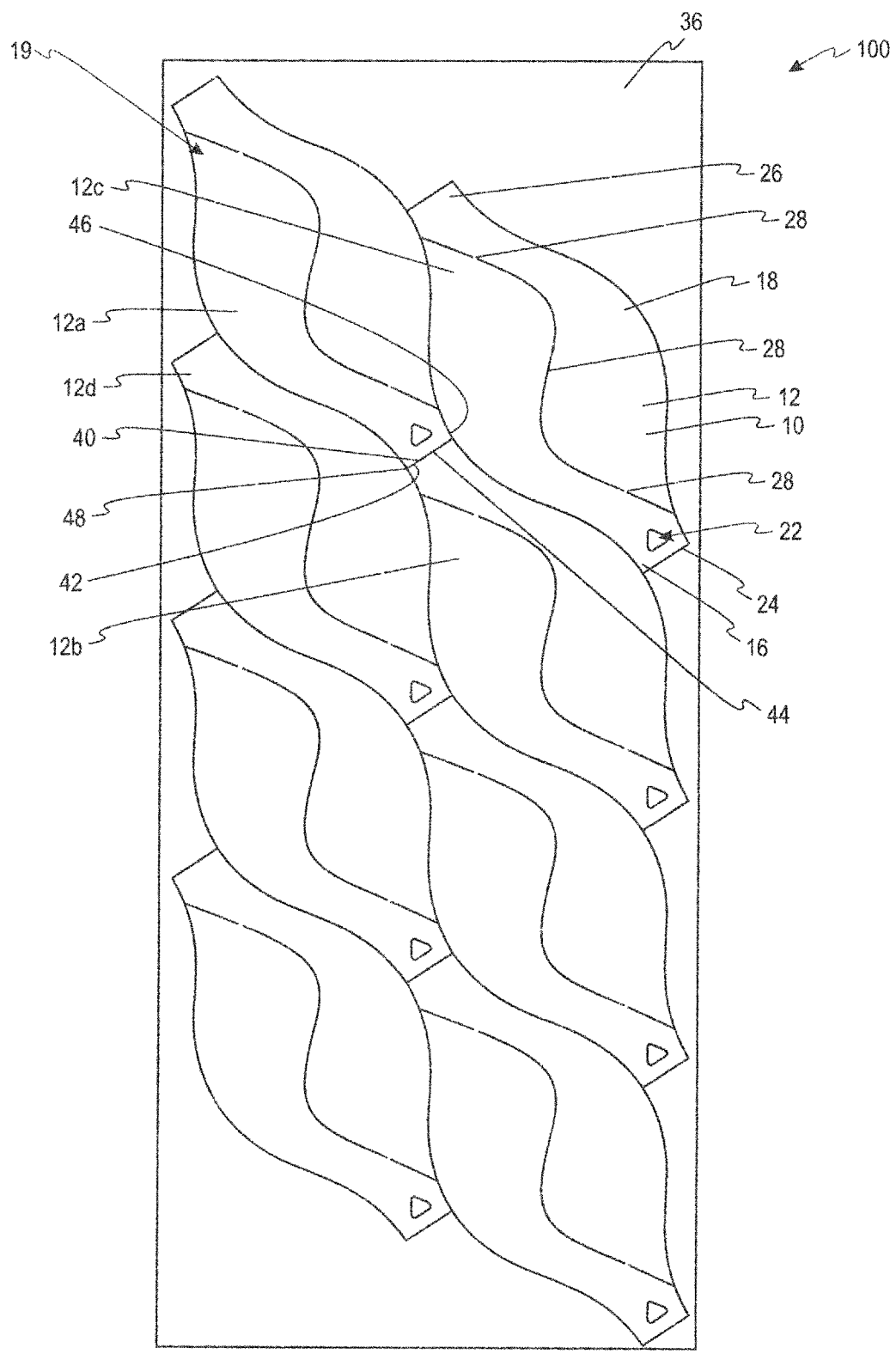
FIG. 10 is a top plan view of a blank sheet of volatile material dispenser substrates according to one embodiment.

In another embodiment, the substrate 12 may vary in size, however, the outline of the substrate may be shaped in such a way such that the substrate tessellates, or fits together without gaps, with one or more adjacent substrates, as seen in FIG. 10. In one particular embodiment, the substrate 12 may have a curvilinear form that combines curved portions and straight lines. Tessellated dispensing devices 10 combine the advantages of efficient manufacturing parameters with aesthetically pleasing shapes. Moreover, these features in concert with articulating dispensing devices 10 that transform from a first state to a second state provide more sophisticated dispensing devices that require little to no material waste for manufacture and improved volatile material delivery. Further, greater manufacturing efficiency may be achieved by using tessellated substrates 12, as are seen in FIG. 10. Here, a blank sheet 100 (i.e., a single or monolithic sheet 36 of substrate material, such as paperboard) is shown that includes several substrates 12 outlined thereon of similar design to those in FIGS. 1-9. The outline of each substrate 12 is tessellated with each adjacent substrate.

Tessellation maximizes use of the blank sheet 100 and minimizes waste. In fact, no waste of material occurs between adjacent substrates 12. For example, as can be seen in FIG. 10, a top end 40 of a first substrate 12a abuts a bottom end 42 of a second substrate 12b to form an intersect 44. The intersect 44 is adjacent a sidewall 46 of a third substrate 12c and another sidewall 48 of a fourth substrate 12d and may be coaxial with the major width axis W of the substrates 12c and 12d. Between the top end 40, bottom end 42, and sidewalls 46 and 48, no portion of the blank sheet 100 is unused. In the embodiment shown in FIG. 10, a total of eight substrates 12 are shown to tessellate with the substrates immediately adjacent on the blank sheet 100, though more or fewer could be arranged on a blank sheet by varying the size and/or outline of the substrates. Therefore, it is apparent that the substrates may be assembled from the blank sheet without waste of material between adjacent substrates (no portion of the blank sheet between substrates goes unused). Moreover, the tessellated outlines enable fewer manufacturing steps, as one cut creates at least two sides of two substrates 12. Still further, each feature of each substrate 12 of the blank sheet 100 may be outlined at one time prior to assembly/manufacture (for example, via die cutting or other process) to further reduce manufacturing steps and minimize waste.

Figure 12:
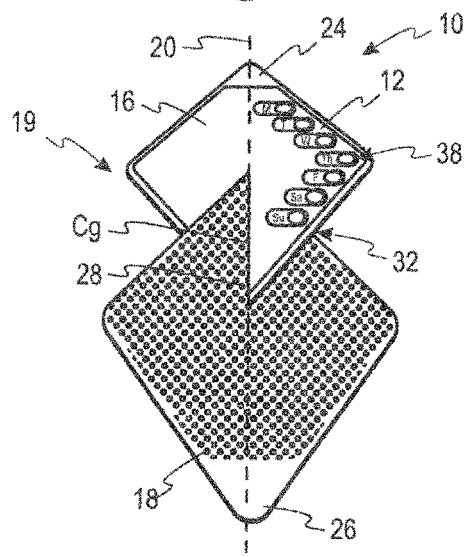
FIG. 12 is a front, bottom isometric view of a dispenser according to another embodiment in a first state.
Figure 12A:
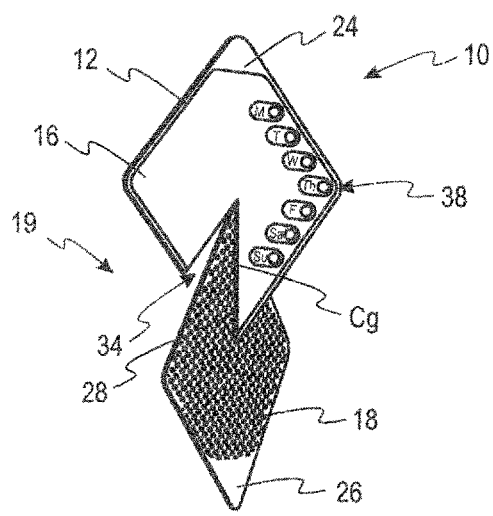
FIG. 12A is a front elevational view of the dispenser of FIG. 12 in a second state.
Figure 13:
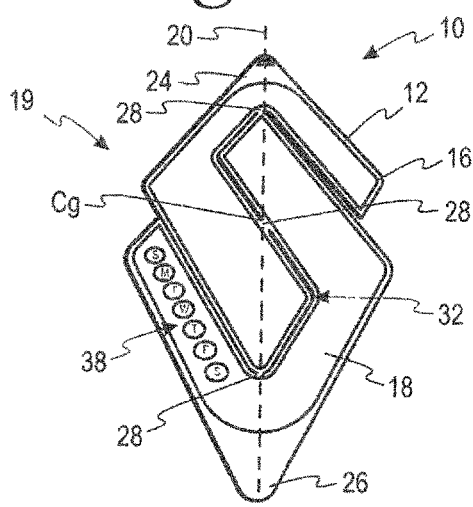
FIG. 13 is a front, bottom isometric view of a dispenser according to another embodiment in a first state.
Figure 13A:
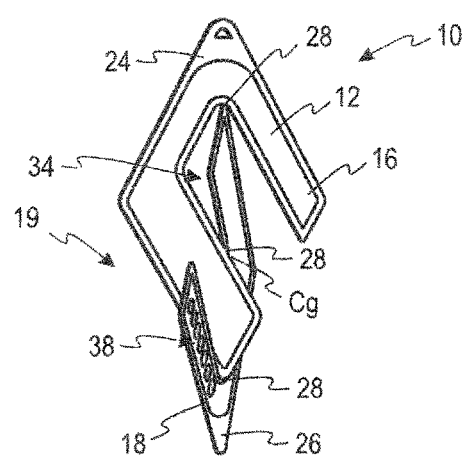
FIG. 13A is a front elevational view of the dispenser of FIG. 13 in a second state.

Additional tessellating forms are contemplated herein, such as those seen in FIGS. 11-13A. Here, three additional dispensing devices 10 with tessellated substrates 12 are shown in the first state (FIGS. 11, 12, and 13) and the second state (FIGS. 11A, 12A, and 13A). These dispensing devices 10 share similar features with those depicted in FIGS. 1-10. However, in contrast to the curvilinear-form dispensing devices 10 shown in FIGS. 1-10, these dispensing devices 10 further include a static center of gravity (Cg) that remains coincident with the central axis 20 (and also does not move along the central axis) when the dispensing devices are disposed vertically in either the first or the second state.

Figure 11:
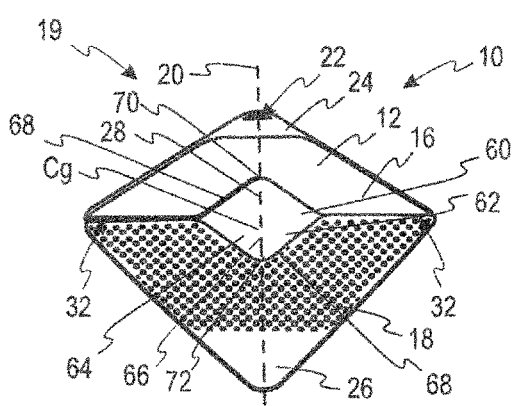
FIG. 11 is a front, bottom isometric view of a dispenser according to another embodiment in a first state.
Figure 11A:
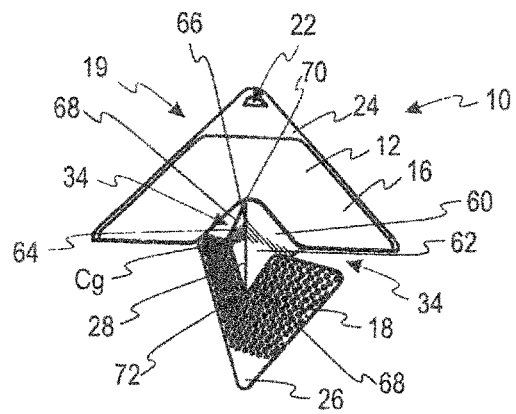
FIG. 11A is a front elevational view of the dispenser of FIG. 11 in a second state.

Referring to FIGS. 11 and 11A, a foldable member 60 is provided between the first wall portion 16 and the second wall portion 18. The foldable member 60 may include a first arm 62 and a second arm 64 joined along a fold line 66, and may be operable to receive the volatile composition or active. In some embodiments, the foldable member 60 allows for passive emanation of the volatile active into the surrounding environment. In a first state (FIG. 11), the foldable member 60 is co-planar with the first wall portion 16 and the second wall portion 18. In a second state, as shown in FIG. 11A, the foldable member 60 is not co-planar with one or both of the first wall portion 16 and the second wall portion 18. More specifically, either one or both of the first arm 62 and the second arm 64 may be not co-planar with the first wall portion 16 and the second wall portion 18 in the second state. In some embodiments, the first arm 62 is equal in size to the second arm 64. In a preferred embodiment, the fold line 66 bisects the foldable member evenly so that the first arm 62 and the second arm 64 are of equal size. The foldable member 60 may be broken away from the body 19 along one or more perforated or die-cut lines 68.

Still referring to FIGS. 11 and 11A, the foldable member 60 is connected with the body 19 of the substrate 12, i.e., the first portion 16 and the second portion 18, at a first hinge point 70 and a second hinge point 72, respectively. The foldable member 60 is rotatable about the axis 20, which is coaxial with the first hinge point 70 and the second hinge point 72. The foldable member 60 may be rotated up to 180 degrees from the first state to the second state about the fold line 66 that is also coaxial with the first hinge point 70, the second hinge point 72, and the axis 20.

The foldable member 60 may be movable between the first state (FIG. 11), when portions of the foldable member 60 are co-planar with the first portion 16 and the second portion 18, and the second state, when the foldable member 60 is moved from the first state and is no longer co-planar with one or more of the first portion 16 and the second portion 18. In a preferred example, the foldable member 60 is rotated 180 degrees from the first state to the second state and both of the first arm 62 and the second arm 64 are not co-planar with the first portion 16 and the second portion 18.

The foldable member 60 may be dosed with a volatile composition or active, such as a pest control agent and/or fragrance, by applying the liquid composition onto the foldable member 60 and/or the first and second wall portions 16, 18. Thereafter, the liquid composition is absorbed into the portion of the body 19, and passively emanated into the ambient environment over a period of time. The intensity of the fragrance may be adjusted by providing more or less fragrance onto the portion of the body 19.

Contemplated dispensing devices 10 may further include text 38 on either or both of the first 16 or second 18 wall portions and also on a front and/or back surface of the dispensing device 10. In one example, the text 38 may include one or more of an instruction, a label, a description of the dispenser's materials, contents, and/or fragrance, a calendar that allows a user to record a day and/or date of initial use and record the number of days of use, an advertisement, an indication of the dispenser's effective lifespan, an indicium, an icon, a picture, a logo, a description of the insects that are effectively repelled and/or killed by the dispenser, a disease claim that indicates the type of disease-carrying insects the dispenser repels and/or kills, a country indicator that indicates in which countries the dispenser may be maximally effective, a brand name, a product name, a product descriptor, a caution, an avatar, and combinations thereof.

In one embodiment, the text 38 may include instructions that direct a user to open a container (not shown) in which the dispensing device 10 is carried, such as a pouch, box, can, or other package, remove the dispenser from the container to activate the dispenser, identify a space to place the activated dispenser, and place the activated dispenser substantially in the center of the identified space, such as an indoor area, a room, a hall, a closet, a porch, and the like. The text 38 may further include instructions that direct a user to record an initial date of use of the dispensing device 10 on the device, such as on a calendar disposed thereon, allow a period of time to elapse for the dispensing device to reach full strength, and leave the dispensing device in the space for a specified period of time from the initial date of use. For example, the instructions may direct the user to use the dispensing device 10 for about 7 days. Further, instructions may direct a user to replace the dispensing device 10 with a new dispensing device after the effective lifespan has passed. Moreover, the instructions may direct the user to use the dispensing device 10 in a room with a fan or in an area with air flow.

INDUSTRIAL APPLICABILITY

The dispensing devices described herein advantageously combine the functional characteristics of an active dispenser that is adjustable between first and second states to maximize the dispenser surface area exposed to air flow during use, without requiring unnecessary waste of materials and excessive manufacturing steps.

Numerous modifications will be apparent to those skilled in the art in view of the foregoing description. Accordingly, this description is to be construed as illustrative only and is presented for the purpose of enabling those skilled in the art to make and use the invention and to teach the best mode of carrying out same. The exclusive rights to all modifications which come within the scope of the application are reserved. All patents and publications are incorporated by reference.

I claim:

1. An emanating device, comprising:
   a substrate, comprising:
      a body having a first portion and a second portion;
      at least one hinge that is disposed along a longitudinal axis of the body and is connected to the first and second portions,
      wherein the body is movable between a first state, such that the first portion and the second portion are co-planar and are connected via at least one attachment point at a location exclusive of the longitudinal axis, and a second state, such that the first portion is not co-planar with the second portion, and
      wherein moving the body from the first state to the second state breaks the at least one attachment point and creates at least one void space in the body.

2. The emanating device of claim 1, wherein the at least one void space is a first void space that is at least partially defined by a first periphery of the first portion and the at least one hinge.

3. The emanating device of claim 2, wherein the at least one void space further includes a second void space that is at least partially defined by a second periphery of the second portion and the at least one hinge.

4. The emanating device of claim 2, wherein the at least one attachment point comprises a perforation.

5. The emanating device of claim 2, wherein the at least one attachment point comprises an adhesive.

6. The emanating device of claim 2, wherein the body is die cut from the substrate.

7. The emanating device of claim 1, wherein the substrate comprises an absorbent substrate.

8. The emanating device of claim 7, wherein the absorbent substrate comprises a cellulosic material, a plastic, a polymer, a fabric, a non-woven substrate, and combinations thereof.

9. The emanating device of claim 7, wherein the absorbent substrate comprises paper-board.

10. The emanating device of claim 7 including a volatile active on at least one of the first and second portions, which allows for passive emanation of the volatile active into the surrounding environment.

11. The emanating device of claim 10, wherein the volatile active includes a fragrance.

12. An emanating device, comprising:
a substrate, comprising:
a first portion; and
a second portion,
wherein the substrate includes a hinge that is co-axial with a longitudinal axis of the substrate, and
wherein in a first state:
the first portion-is co-planar with the second portion, and the first and second portions are connected by at least one attachment point at a location exclusive of the longitudinal axis, and
wherein in a second state:
the first portion is not co-planar with the second portion.

13. The emanating device of claim 12, wherein the first portion is connected to the second portion at the hinge.

14. The emanating device of claim 13, wherein in the second state, a first void space is at least partially defined by a first periphery of the first portion and the hinge.

15. The emanating device of claim 14, wherein in the second state, a second void space is at least partially defined by a second periphery of the second portion and the hinge.

16. The emanating device of claim 15, wherein the first void space is equal in size to the second void space.

17. The emanating device of claim 13, wherein the substrate is die cut.

18. An emanating device, comprising:
an absorbent substrate, which comprises:
a body having a porous cellulosic material for absorption of a volatile active, and further including a first portion and a second portion; and
at least one hinge provided on a longitudinal axis of the body and connected to the first and second portions,
wherein the body is movable between a first state, such that the first portion is co-planar with the second portion, the first portion being connected to the second portion via at least one attachment point at a location exclusive of the longitudinal axis, and a second state, such that the first portion is not co-planar with the second portion.

19. The emanating device of claim 18, wherein moving the body from the first state to the second state breaks the at least one attachment point and creates at least one void space.

20. The emanating device of claim 19, wherein the at least one attachment point comprises a perforation.

* * * * *